(12) United States Patent
Ribbing et al.

(10) Patent No.: US 8,929,625 B2
(45) Date of Patent: Jan. 6, 2015

(54) METHOD AND DEVICE FOR SIDE-EFFECT PROGNOSIS AND MONITORING

(75) Inventors: Carolina Ribbing, Aachen (DE); Martin Weibrecht, Aachen (DE); Peter Klaus Bachmann, Wuerselen (DE); Michael Perkuhn, Bocholtz (NL); Marco Daniel Pascal Lierfeld, Erkelenz (DE); Michael Pinkawa, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 312 days.

(21) Appl. No.: 13/321,873

(22) PCT Filed: May 21, 2010

(86) PCT No.: PCT/IB2010/052266
§ 371 (c)(1),
(2), (4) Date: Nov. 22, 2011

(87) PCT Pub. No.: WO2010/136942
PCT Pub. Date: Dec. 2, 2010

(65) Prior Publication Data
US 2012/0063657 A1    Mar. 15, 2012

(30) Foreign Application Priority Data
May 28, 2009 (EP) .................... 09161384

(51) Int. Cl.
*G06K 9/00* (2006.01)
*G06F 19/00* (2011.01)
*A61N 5/10* (2006.01)
(52) U.S. Cl.
CPC ............ *A61N 5/103* (2013.01); *G06F 19/3481* (2013.01)

USPC .......................................... 382/128

(58) Field of Classification Search
None
See application file for complete search history.

(56) References Cited

U.S. PATENT DOCUMENTS

| | | | |
|---|---|---|---|
| 5,572,421 A | 11/1996 | Altman et al. | |
| 6,607,482 B1 | 8/2003 | Teitelbaum | |
| 7,056,289 B2 | 6/2006 | Kasper et al. | |
| 7,461,048 B2 | 12/2008 | Teverovskiy et al. | |

FOREIGN PATENT DOCUMENTS

| | | |
|---|---|---|
| EP | 1953662 A1 | 8/2008 |
| WO | 0209004 A1 | 1/2002 |
| WO | 02096284 A1 | 12/2002 |
| WO | 2004105574 A2 | 12/2004 |
| WO | 2008025662 A2 | 3/2008 |
| WO | 2008035286 A2 | 3/2008 |

OTHER PUBLICATIONS

Terry N H A et al: "Cellular Kinetics of Murine Lung: Model System to Determine Basis for Radioprotection With Keratinocyte Growth Factor" International Journal of Radiation Oncology Biology Physics Elsevier USA, vol. 58, No. 2, Feb. 1, 2004, pp. 435-444, XP002607857 ISSN: 0360-3016 the whole document.

(Continued)

*Primary Examiner* — Nirav G Patel
*Assistant Examiner* — Amandeep Saini (57) ABSTRACT

A method for radiotherapy monitoring is provided. The method comprises calculation of treatment-guiding indices of side-effects based on processing image derived descriptors and measurement values of selected disease specific biomarkers and optionally questionnaire data. A computer program product is also provided.

11 Claims, 2 Drawing Sheets (56) References Cited

OTHER PUBLICATIONS

Ahn Jiyoung et al: "Polymorphisms in genes related to oxidative stress (CAT, MnSOD, MPO, and eNOS) and acute toxicities from radiation therapy following lumpectomy for breast cancer." Clinical Cancer Research : An Official Journal of the American Association for Cancer Research Dec. 1, 2006 LNKDPUBMED: 17145829, vol. 12, No. 23, Dec. 1, 2006, pp. 7063-7070, XP002607858 ISSN: 1078-0432 the whole document.

Svensson, J.P. et al. "Analysis of gene expression using gene sets discriminates cancer patients with and without late radiation toxicity", PLoS Medicine, Oct. 2006, vol. 3, Issue 10.

Kruse, J. et al. "Gene expression arrays as a tool to unravel mechanisms of normal tissue radiation injury and prediction of response". World J Gastroenterol 2007; 13(19): 2669-2674. May 2007.

Pinkawa, M. et al. Low-grade toxicity after conformal radiation therapy for prostate cancer—impact of bladder volume, Int J Radiat Oncol Biol Phys. Mar. 1, 2006;64(3):835-41.

Pinkawa, M. et al. "Prostate position variability and dose-vol. histograms in radiotherapy for prostate cancer with full and empty bladder". Int J Radiat Oncol Biol Phys. Mar. 1, 2006;64(3):856-61.

Shonde A. et al, "The role of radiological imaging in the patient with gastrointestinal symptoms after pelvic radiotherapy". Cancer Imaging. 2004; 4(2): 92-94. Feb, 2004.

Patterson, D.M. et al. "Technology Insight: water diffusion Mri—a potential new biomarker of response to cancer therapy", Nature Clinical Practice Oncology (2008) 5, 220-233. Oct , 2008.

Christiansen, H. et al. "Increase of hepcidine plasma and urine levels is associated with acute proctitis and changes in hemoglobin levels in primary radiotherapy for prostate cancer", J Canc Res Clin Oncol (2007 133:297-304. Nov. 2006.

Menard, C. et al, "Discovering clinical biomarkers of ionizing radiation exposure with serum proteomic analysis", Cancer Res 2006; 66: (3). Feb. 1, 2006.

Radiation Therapy Oncology Group. http://www.rtog.org/ Dec. 1996.

SPSS, Data Mining, statistical Analysis Softward, Predictive Anal. pages 3-7. SPSS.com Jan. 2008.

Munbodh, R. et al. "Dosimetric and anatomic indicators of late rectal toxicity after high-dose intensity modulated radiation therapy for prostate cancer". Medical Physics, vol. 35, No. 5, May 2008, pp. 2037-2150.

MYSQL Reference Manual: 1.3.1, pp. 3-5. http://www.mysq.com/ Jan. 1995.

Horacek, J.M. et al. "Multiple biomarkers in the assessment of cardiac toxicity during haematopoietic stem cell transplantation in acute leukaemia". Bone Marrow Transplantation 41S100-S100 2008. 34th Annual Meeting of the European Group for Blood and Marrow Transplantation. Mar. 30-Apr. 2, 2008 in Florence, Italy.

METHOD AND DEVICE FOR SIDE-EFFECT PROGNOSIS AND MONITORING

FIELD OF THE INVENTION

This invention pertains in general to the field of medical imaging. More particularly, the present invention pertains to a method for calculation of treatment-guiding indices of side-effects based on medical imaging data combined with e.g. in vitro diagnostic data.

BACKGROUND OF THE INVENTION

Prostate cancer is the most common cancer in men and the number of new cases is increasing. For example in US this prostate cancer affects approximately 230000 patients per year. However, in most cases, the cancer is a slowly developing disease and the 5-year survival is about 90%. There are several treatment options with different impact on patient quality of life. The decision and management processes of prostate cancer treatment are complex and involve a delicate balance between optimization of clinical benefits, life expectancy and minimization of treatment-related side-effects.

In total approximately four out of 10 cancer patients receive radiotherapy as part of their treatment. The damage of normal tissue leads to acute side-effects that often turn into chronic problems.

Basic treatment options for prostate cancer are watchful waiting, radical prostatectomy, and radiotherapy. Radiation as first line treatment is applied in about 50% of all prostate cancer cases. Recurrent disease is almost completely treated with radiotherapy. Radiation is delivered in several fractions, most often daily over a period of several weeks, e.g. 76 Gy in 38 fractions over 8 weeks. Radiotherapeutic treatment options include external beam therapy (EBT), e.g. conformal radiation therapy where the radiation is delivered to the diseased area while attempting to spare surrounding tissue. Radiation therapy procedures include 3D conformal radiation therapy and intensity modulated radiation therapy (IMRT). An alternative to EBT is brachytherapy, which uses seeds of radioactive isotopes that are temporary or permanently implanted into the prostate. Temporary implantation is done with high dose rate (HDR) sources, e.g. Ir-192, often in combination with EBT. Permanent implantation uses low dose rate (LDR) seeds, e.g. Pd-103. In general, brachytherapy results in a lower dose to surrounding healthy tissue and risk organs, giving less severe side-effects of the radiation treatment.

Radiotherapy plays an important role in other cancer types as well. In the developed countries, 80% of lung cancer patients, 75% of breast cancer patients, and all head and neck cancers are treated with radiation therapy.

The maximum radiation dose that can be given is limited by the tolerance of normal tissues within the radiation field. The radiation response varies considerably between individuals and the tolerance of the most sensitive subjects limits the dose that can be given to the population as a whole, which may limit the chance of tumor cure. Ionizing radiation induces orchestrated response cascades at cellular as well as tissue level. The responses involve differential regulation of several cytokine cascades, which together impact the resulting normal tissue damage. Radiation-induced damage of normal tissue involves many different cell types and the long-term tissue composition is likely to change as a result of radiation. For example, the amount of inflammatory cells and fibrotic tissue increases after irradiation.

Genetic microarrays have been used for radiotoxicity prognosis, i.e. to generate gene signatures identifying radiotoxicity sensitive and resistant populations. Furthermore, microarray techniques have also been employed for mechanistic purposes, i.e. to identify genes and pathways involved in tissue injury response. In interpretation of microarray results, care has to be taken. The methodology is still immature for clinical routine use. Inconsistencies between different microarray platforms make it almost impossible to compare independently obtained data sets addressing the same biological problem. Also, probe sequence information was until now most often not provided for commercially available microarrays. It has been shown that genetic changes from radiotherapy can be detected in peripheral blood cells (circulating lymphocytes) and that these changes correlate with development of acute toxicity. Also, gene expression profiles for in vitro irradiated lymphocytes correlate with acute or late radiation injury.

Before radiation treatment of prostate cancer starts, the patient is normally imaged using various techniques. Needle biopsies are most often taken under transrectal ultrasound (TRUS) guidance. However, the TRUS image contrast is not high enough for detection of early-stage prostate cancer. For staging of more advanced prostate cancer, anatomical imaging modalities like x-ray computed tomography (CT) and magnetic resonance imaging (MRI) can be used, e.g. to detect extra-capsular tumor extensions, seminal vesicle involvement, and abnormal sizes of lymph nodes. Functional imaging modalities can also be employed, e.g. positron-emission tomography (PET) using choline tracers, single-photon emission computed tomography (SPECT), and special MR schemes (MR spectroscopy, Combidex® for lymph-node staging). Finally, for planning and simulation of the radiotherapy, a planning CT scan is made, tumor and sensitive organs are outlined on axial slices, and the geometric centre of the tumor volume is calculated.

Local control of a tumor increases with the administered radiation dose. However, by increasing the radiation dose, the risk of complications increases. In the case of prostate cancer, the primary risk organs and structures are bladder, urethra, rectum, seminal vesicles and associated nerve bundles controlling sexual function. The incidence of complications is also associated with the size of the irradiated volume. There are several ways to assess such so-called radiation toxicity. These include physician-reported instruments, e.g. the RTOG acute and late toxicity questionnaires, EORTC, the Royal Marsden Scale that measures symptom frequency, and the LENT/SOM questionnaires. Additionally, there are patient-reported quality of life questionnaires like MOS SF-36, UCLA Prostate Cancer Index, the expanded prostate cancer index composite (EPIC), and FACT-P.

There are several predictors of radiation toxicity. For example, the mean rectal dose correlates with acute rectal and intestinal toxicity in 3D conformal radiotherapy of prostate cancer, whereas hormonal therapy and the use of anticoagulants are protective. More precisely, a larger mean rectal dose is associated with a larger bleeding risk, larger irradiated volumes are associated with stool frequency, tenesmus, incontinence, and bleeding. Hormonal therapy is protective against frequency and tenesmus; hemorrhoids are associated with a larger risk of tenesmus and bleeding, and diabetes associate with diarrhea. The dose to the rectal wall can be analyzed in more detail by use of dose-volume histograms (DVH) from 3D treatment planning systems. By such analysis, the volume of rectal wall receiving the highest dose (e.g. the wall volume receiving >70Gy), the irradiated rectum area, target and rectum size may in some cases be more predictive of late rectal toxicity than the mean rectal dose. Target volume and height, rectum surface area and average cross-sectional area have also been shown to correlate with toxicity. The bladder volume and the percentage of the bladder volume that receives 10-90% of the prescribed dose are correlated with urinary function and patient questionnaire bother scores. Furthermore, a full bladder improves the position consistency of the prostate and lowers the bladder and bowel doses.

The prostate is situated between the bladder and the rectum, both radiosensitive organs. During radiotherapy, most prostate cancer patients develop acute side-effects from radiation damage in surrounding organs, e.g. diarrhea, rectal bleeding, abdominal cramps, tenesmus, impotence, fecal or urinary incontinence. According to a recent study, approximately 80% of patients receiving pelvic radiotherapy developed gastrointestinal problems. In some patients, radio-damage of normal tissue even leads to chronic gastrointestinal problems or impotence. Obviously, both acute and late radiotoxicity effects have severe impact on patients' quality of life. Furthermore, very severe acute side-effects may lead to discontinuance of radiotherapy, resulting in impaired tumor control.

Therapy monitoring and individual therapy adjustment are important issues. As described, individuals are significantly affected by impaired quality-of-life and limited tumor control. Regarding healthcare costs, acute and especially chronic side-effects due to radiation damage require considerable treatment. Hence, reducing (or even avoiding) side-effects early in the cancer treatment may save expenditures on side-effect treatment.

Thus, there is a need for a method and a device for monitoring side-effects of radiation treatment.

The present inventors have realized that there is no single biomarker of side-effects and radiotoxicity. Therefore an idea is to utilize information provided by multiple biomarkers jointly.

A general idea of the present invention is to combine parameters obtained from morphology, from metabolic, functional, physiological, or pharmacological characteristics and therapy parameters, and subsequently evaluate and/or prognosticate disease status including side-effects. The resulting information may be used to adapt therapy.

Moreover, an idea is to process a combination of medical imaging features with in vitro diagnostics (IVD) data in order to calculate an output signal being indicative of the radiotoxicity in an area of the tissue of interest. Particularly advantageous is the combination of image-derived features with information provided by molecular biomarkers, information on concomitant medication, and anamnesis.

An object is to provide a method for therapy monitoring, particularly for diagnosing radiotoxicity and adapting radiotherapy depending on the level of radiotoxicity.

Another object is to provide a method, which combines the information provided by imaging with the information provided by molecular biomarkers to deduce a measure of radiotoxicity for treatment adjustment and optimization.

Moreover, data from a patient questionnaire may be utilized in deducing the measure of radiotoxicity.

According to an aspect a method for radiotherapy monitoring is provided. The method comprises obtaining at least one image derived descriptor from an image modality, wherein the image derived descriptor pertains to a tissue of interest for which radiotherapy is planned or a tissue in the vicinity of this target volume. The method further comprises selecting at least one disease specific biomarker suitable for detecting or quantifying radiotherapy side-effects in the area of the tissue of interest. Furthermore, the method comprises retrieving at least one measurement value of the selected disease specific in vitro diagnostic biomarker. Moreover, the method comprises processing the at least one image derived descriptor and the at least one disease specific in vitro diagnostic biomarker measurement value by means of a correlation technique, resulting in an output signal indicative of the radiotoxicity in the area of the tissue of interest.

The method according to some embodiments takes into account a set of parameters, such as the size of tumor target and genetic profiles, which have prognostic value. The analysis of such parameters allows for estimating the risk to develop side-effects for a given treatment, in particular for radiotherapy. Hence, the method may also be utilized as prognostic tool in treatment decisions even before radiation treatment is actually employed or started.

The method provides for optimized radiotherapy planning, early detection of radiotoxicity and concomitant dose adjustment which may help minimizing complications while keeping target dose as high as possible. In particular, side-effect preventive measures may be taken at an early point in time during radiotherapy.

In another aspect a computer program product is provided, wherein the computer program product having embodied thereon a computer program for processing by a data-processing apparatus. The computer program comprises a first code segment for obtaining at least one image-derived descriptor from an image modality, wherein the image derived descriptor pertains to a tissue of interest for which radiotherapy is planned. The computer program further comprises a second code segment for selecting at least one disease specific biomarker suitable for detecting or quantifying radiotherapy side-effects in the area of the tissue of interest. Moreover, the computer program comprises a third code segment for retrieving at least one measurement value of the selected disease specific in vitro diagnostic biomarker. Furthermore, the computer program comprises a fourth code segment for processing the at least one image derived descriptor and the at least one disease specific in vitro diagnostic biomarker measurement value by means of a correlation technique, resulting in an output signal indicative of the radiotoxicity in the area of the tissue of interest.

According to another aspect a method for producing an individual patient profile is provided. The method comprises inputting data comprising individual patient answers to multiple-choice questions of a medical questionnaire. Moreover, the method comprises storing the answers forming an individual patient profile comprising the answer selection excluding the actual question text. The method further comprises storing information of the questionnaire version presented to the patient and the date of questionnaire completion in the data file. Furthermore, the method comprises creating an individual patient profile report by applying a profile processing algorithm on the information of the data file, such as at least one of the answers. The method further comprises displaying the individual patient profile report on a display device.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

The following description focuses on an embodiment of the present invention applicable to a method for radiotherapy planning, and in particular to a method for side-effect prognosis and monitoring of radiation treatment.

Figure 1:
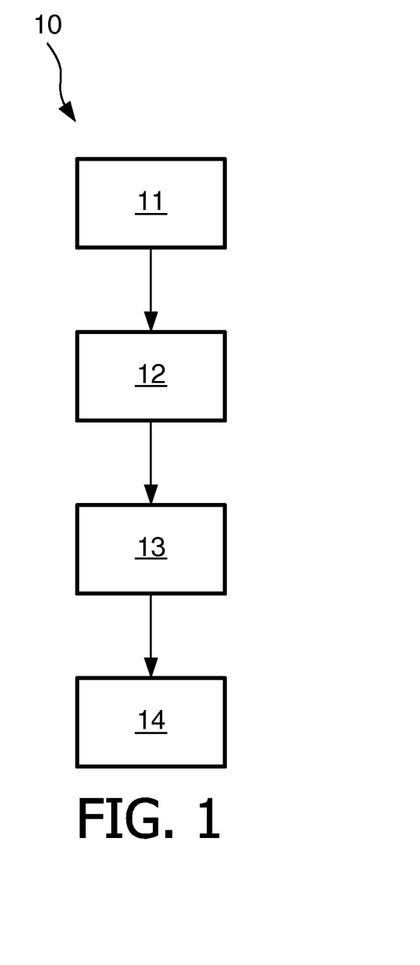
FIG. 1 is a flow chart of a method according to an embodiment.

In an embodiment, according to FIG. 1, a method 10 for radiotherapy monitoring is provided. The method comprises obtaining 11 at least one image descriptor derived from an image modality, wherein the image derived descriptor pertains to a tissue of interest for which radiotherapy is planned, resulting in a first feature vector. Moreover, the method comprises selecting 12 at least one disease specific biomarker suitable for detecting or quantifying radiotherapy side-effects in the area of the tissue of interest. Furthermore, the method comprises retrieving 13 at least one measurement value of the at least one selected disease specific biomarker, resulting in a second set of feature vectors. The method further comprises processing 14 the at least one image derived descriptor and the at least one disease specific biomarker measurement value by means of a correlation technique, resulting in an output signal indicative of the radiotoxicity in the area of the tissue of interest.

In an embodiment, several image derived descriptors are obtained during the step of obtaining 11. Hence, the step of obtaining 11 comprises obtaining a set of image derived descriptors.

In an embodiment, several disease specific biomarkers are selected during the selection step 12, and thus several measurement values are retrieved in the step of retrieving 13. Hence the step of selecting 12 comprises selecting a set of disease specific biomarkers.

In an embodiment the step of obtaining 11 further comprises creating a first feature vector comprising the obtained image derived descriptors, and the step of retrieving 13 comprises creating a second feature vector comprising the retrieved selected disease specific biomarker measurement values.

The term "disease specific" should be interpreted as to encompass the term "radiotoxicity specific".

For example, in an embodiment, the step of obtaining the set of image derived descriptors may comprise, extracting a first image derived descriptor pertaining to the dose to the rectal wall, and a second image derived descriptor pertaining to the irradiated volume, from planning Computed Tomography (CT) and simulation tools.

In an embodiment, Hb, and pro-hepcidin are selected in the step of selecting a set of disease specific biomarkers. These biomarkers are measured, in a way well known in clinical laboratories, in the step of retrieving 13. A protective factor may using commonly known methods be formed by subtracting constants less than one and characteristic of anticoagulant and hormone dose from unity.

The processing step 14 may e.g. then comprise multiplying a product of the concentrations of the biomarkers by the rectal wall dose, the irradiated volume, and the protective factor to derive an index indicative of grade of radiotoxicity. The index may be incorporated in an output signal suitable for further analysis or presentation e.g. before a physician on a display device.

In an embodiment, an IVD test can be performed to assay early radiotoxicity. Example: an IVD test value may be multiplied by an imaging descriptor, e.g. dose to a certain volume, to provide an index which is indicative of radiotoxicity.

Imaging descriptors provide morphological information on e.g. volumes of tumor and surrounding organs, and may also include radiotherapy dose statistics, e.g. dose volume histograms (DVHs). Functional information, e.g. bowel function and/or perfusion, as well as molecular information, e.g. metabolism, can be assessed by appropriate imaging modalities and tracers, e.g. FDG-PET.

More in detail, typical image descriptors are features extracted from pelvic MRI and/or radiotherapy planning CTs, including bladder and rectum volumes, morphological distances, dose to the rectal wall, various mean doses, and DVHs. T2-weighted MRI, for instance, is particularly useful in pelvic regions to monitor changes due to inflammation, e.g. edema in the rectal wall. Of course, imaging descriptors from other imaging modalities may also be used, e.g. features extracted from US, SPECT or PET. In particular, diffusion-weighted MRI may be useful for characterization of tumor malignancy, for therapy monitoring, for assessing inflammatory processes and to diagnose early stages of radiation-induced fibrosis. Several image feature extraction algorithms, which are known, could be used in conjunction with the method according to some embodiments.

In an embodiment the set of image descriptors is selected from the group comprising: macroscopic tumor volume; risk organ; volumetric information either directly assessed by the imaging modality, e.g. Hounsfield units of CT data or dose deposition volumes calculated by the radiotherapy planning software, or indirectly assessed by the imaging modality, e.g. parametric maps derived from dynamic imaging sequences like perfusion data derived from dynamic contrast enhanced MRI (DCE-MRI) or dynamic PET imaging.

In an embodiment an image descriptor is a feature vector constituting a three- or four-dimensional matrix derived from the available image data. Feature vectors derived from in vitro biomarkers may be as simple as scalar values. They may as well become rather complex, like mass spectra acquired for instance by SELDI-MS.

Additional features for the intended analysis may be derived from, e.g. the prescribed dose and the treatment procedure, e.g. intensity modulated radiation therapy (IMRT).

In an embodiment patient morphology in the pelvic region is utilized when calculating the output signal indicative of the radiotoxicity. For example, morphological features, such as distance between prostate (or the surgical bed after its removal) and the intestinal wall or the bladder or other organs in the pelvic region define the size of the irradiated field, possible unwanted dose to organs/areas close to the radiation target region, and thus corresponding side-effects. The closer a sensitive organ/tissue is to the target tissue (tumor and lining) the higher the dose to the sensitive tissue. Therefore, such a morphological feature may be used to predict the radiotoxicity of the tissue of interest.

In an embodiment, pre-therapy pelvic morphology, e.g. imaged by T2w MRI, is classified and quantified, and compared in terms of overall dose and dose-volume histograms for the prostate and rectum and side-effect profile resulting from radiotherapy in the processing step 14. In this way, e.g. edema in the pelvic region may be assessed by T2w MRI at defined intervals during therapy, classified and quantified, and correlated to toxicity.

In an embodiment, the use of morphological and functional imaging before and during radiotherapy may allow to reduce toxicity. Morphological and functional parameters of the prostate may be assessed by T2w MRI, choline PET, MR spectroscopy or diffusion-weighted MR before and at defined intervals during therapy. This information may be used to simulate differences in overall dose and dose-volume histograms for the prostate and rectum that would result from image-based adaption of the radiotherapy plan at the beginning of, and the given intervals during, therapy. The simulated plan may be modulated so as to concentrate dose in prostate regions where morphological/functional imaging suggests malignancy while reducing dose in regions identified as benign. The use of multiple imaging methods may allow a cross-validation of findings and a comparison of methods, in particular between choline-PET and MR spectroscopy.

In terms of the imaging modalities that are advantageously used within the framework of this invention, CT, PET and MR are particularly useful. However, other imaging procedures with and without contrasting agents are also included, e.g. SPECT-, X-ray- and also Optical Imaging.

In an embodiment, the set of image descriptors may be retrieved utilizing known feature extraction techniques.

In an embodiment, the set of disease specific biomarkers include e.g. inflammatory biomarkers based on the rationale that radiation induces inflammation. Moreover, the set of biomarkers may comprise several IVD markers, e.g. a biomarker that is known to indicate epithelial cell loss in the small bowel close to the irradiated area as such a loss is known to be associated with impaired bowel function. Furthermore, the set of biomarkers may comprise TM-C protein (thrombomoduline) that indicates microvascular injuries by radiation. Serum alpha amylase that is produced if certain glands are irradiated (but should not be irradiated) may also be utilized in the set of selected biomarkers.

All of the biomarkers used are selected based on a biomedical disease specific rationale.

In an embodiment, the set of selected disease-specific biomarkers includes genetic information and any products produced or given off as a result of in vivo tissue interaction with ionizing radiation. Radiation-induced expression of pro-inflammatory cytokines and acute phase proteins may be employed to detect side-effects of the ionizing radiation. These biomarkers provide information on physiological side-effects of radiotherapy or radiation sensitivity predisposition by detection of peptides, proteins or nucleic acids. These set of disease specific biomarkers may e.g. include standard in vitro diagnostics (IVD) markers, e.g. haemoglobin concentration (Hb), complete and leukocyte blood cell count, C-reactive protein (CRP), ferritin, transferrin, creatinine, alpha-amylase, HbA1c, TNF-α, lactate dehydrogenase (LDH), and interleukins, e.g. IL-6 or IL-1β. The set of selected disease specific biomarkers may also include less commonly analyzed IVD markers like hepcidin, pro-hepcidin, immunoglobin fragments, citrulline.

In an embodiment, the set of selected disease specific biomarkers comprises mass spectrometric protein signatures which are measured using any bodily fluid or obtained from measurements using tissue samples, especially in the 1-20 kDa mass region, since many diagnostic relevant compounds have a mass in this range. The proteomic, i.e. mass spectrometric, features comprise mass spectrometric peak patterns that are specific for the disease, such as radiotoxicity, in question.

The pro-hepcidin concentration before radiotherapy may be <100 ng/ml in plasma in patients prone to acute proctitis, whereas it may be >100 ng/ml in patients who do not get proctitis from prostate radiotherapy. Corresponding values for urine may be <60 ng/ml and >60 ng/ml, respectively. During radiotherapy, plasma pro-hepcidin levels may rise significantly in patients with acute proctitis but stay relatively constant in patients without proctitis. A similar pattern can be seen in plasma IL-6 and TNF-α concentrations with cutoff values around 0.1 pg/ml and 2 pg/ml, respectively. Hb and leucocyte count may decrease in patients who develop acute proctitis during radiotherapy, e.g. with cutoffs of 14 g/dl and 6100/A respectively. Biomarker concentrations may be quantified by standard ELISA tests, e.g. pro-hepcidine from DRG International (Marburg, Germany), IL-6 from Holzel Diagnostika GmbH (Köln, Germany), and TNF-α with Quantikine® ELISA kit from R&D Systems (Minneapolis, USA). The numerical values given above are to be regarded as approximate only, and may not be diagnostic if used individually, but only in combination with e.g. imaging descriptors.

Genetic biomarkers of radiotoxicity may be assessed using cDNA microarrays. For example, high constitutive expression of DNA repair-related genes seems to be protective for acute side-effects in radiotherapy patients. Potential genes influencing the sensitivity to radiotoxicity include ATM, BRCA1 and 2, ERCC1, FHIT, LIG3, MDM2, MUTYH, PMS2L2 and L9, POLH, POLK, RAD23B, RFC2, TOP3A/2, and TP53. Furthermore, patient telomere length may modulate radiosensitivity. Short telomeres are likely to interfere with repair of DNA double strand breaks in the genome and thus give higher radiosensitivity. Therefore, telomere length data may also be incorporated in a model for prognostic radiation toxicity assessment. Length measurements can be performed using conventional phenol-chloroform DNA extraction and a telomere restriction fragment assay, e.g. the TeloTAGGG Telomere Length Assay Kit from Roche Diagnostics. Individuals with short telomeres, e.g. 7023±427 bp are potentially more radiosensitive than those with longer telomeres, e.g. 9280±263 bp.

In an embodiment, the disease specific biomarker is associated with physiological changes or predisposition of radiotoxicity.

The selected set of biomarkers may be measured using commonly known methods readily available to the skilled person.

The biomarkers may be detected and measured in any suitable sample, for example patient biopsy material, blood, serum, plasma, blood cell culture, urine, faeces, sweat, saliva, sperm, or exhaled breath. The sample may be used as is or be pre-treated prior to the detection or measurement step. The pre-treatment step may be accomplished using standard procedures including chromatography, adsorption, elution, dialysis, ion exchange, centrifugation, coagulation, filtration, precipitation, denaturation, immunostaining, and combinations thereof.

In an embodiment, the step of processing further comprises compressing the first set of feature vectors and/or second set of feature vectors. This is advantageous since complete feature vectors usually are too complex to be analyzed in one step. Compression of the complex image feature vectors can be accomplished by known methods, such as techniques comprising extracting scalars like maximum value, minimum value, median value, mean value and the like. A more complex method is generating histograms. Also techniques utilizing clustering, e.g. K-means clustering, may be used, where the clusters in turn may be compressed by the aforementioned compression schemes, e.g. averaging. Also shape or texture parameters can be derived. Regarding complex in vitro diagnostic data like mass spectra, compression schemes may be the selection of peak values and corresponding masses. Of course, the same approach can also be applied to image-derived histograms in order to reduce complexity further.

In an embodiment, the step of processing further comprises analyzing the compressed first set of feature vectors and/or second set of feature vectors, and based thereon calculating the treatment-guiding indices of the side-effects. Fundamentally, this is a classification that can be performed by any suited classifier algorithm.

The processing step/classification may comprise a cascaded analysis. In an embodiment, the step of processing further comprises composing multiple sub feature vectors from the compressed first and/or second feature vectors, which are analyzed for a scalar result each. In such a way subgroups (e.g. predisposition, actually measured changes) of features of the first and/or second feature vectors are obtained, each sub group comprising at least one feature from the first and/or second feature vector. Each sub group may be composed to be directed to a certain aspect of the radiotherapy. These sub groups may be individually analyzed, e.g. regarding the predisposition, or the actual inflammatory reaction, and subsequently the analysis results may be combined to predict the risk of specific side-effects. By processing the sub feature vectors indices for the combination of features in the sub feature vectors may be obtained. Hence such sub feature indices may be indicative for the certain aspect of the radiotherapy, which is advantageous in some situations.

For instance, in vitro diagnostics features related to prognosis, i.e. baseline data from DNA analysis, telemore length, etc. may be combined in one feature vector from which a scalar IVD risk factor is derived. This can be accomplished by, for instance, multivariate analysis, a neural network or a suited vector norm scaled by a normalization parameter derived from non-symptomatic patients. A second subgroup refers to image-based prognostic features, e.g. dose-volume histograms, volumes of organs and targets, etc. Again, a neural network, a suitable vector norm, or similar means are applied to the image-based prognostic feature vector to derive a scalar value, which represents an image-based risk factor. A third subgroup composes feature vectors that refer to changes relative the baseline measurements. Again this can actually be two subgroups, one composed of IVD data and one composed of image data. The IVD data can refer to proteomic changes like changes in CRP concentrations, lymphocyte counts etc. The image-based feature vectors may refer to (spatially resolved) changes in perfusion as assessed for instance by DCS-MRI. Subsequently, these scalars are analyzed jointly for the final treatment-guiding indices of the side-effects. This can be accomplished by composing a new feature vector from the individual scalars, which is subjected to a suited analysis, for instance by means of a neural network, a vector norm, multivariate analysis, etc. In the simplest realization, the cascade actually collapses to a single analysis by integrating all available compressed feature vectors in a single comprehensive feature vector.

In this form, the processing step 14 comprises performing analysis by means of a multivariate, multidimensional mathematical function involving e.g. division, product, sum, difference, logarithmic function, exponential function or a combination thereof.

Alternatively, the correlation technique used in the processing step 14 may involve a correlation analysis between compressed and/or sub feature vectors. For instance, certain image-based features and certain IVD features associated with inflammation may exhibit prognostic relevance only in combination, i.e. only if both feature values are elevated above normal a certain condition is present (positive correlation). Of course, other correlations, e.g. negative correlations, are possible as well. For instance reduced cell proliferation (assessed for instance by FLT-PET imaging) and increased apoptosis assessed by respective proteomic markers may indicate severe toxicity. Again, multiple correlations may be evaluated for multiple side-effects.

In an embodiment the processing step 14 further comprises processing the set of image derived descriptors and the set of biomarkers together with parameters derived from medication, co-morbidities, or anamnesis.

In an embodiment the step of processing comprises calculating a set of indices at various time points during radiotherapy, and calculating a ratio of the indices being indicative of the radiotoxicity progression.

In an embodiment the step of processing comprises combining at least one image descriptor with at least one biomarker measurement, including medication or anamnetic descriptors, whereby the output signal comprising a combination of the image descriptors and biomarkers may facilitate personalization of the therapy for the patient in question. For example, the output signal may comprise information indicating selection of most appropriate treatment e.g. prostatectomy, radiotherapy including choice of modality, or hormonal treatment.

In an embodiment, the processing step 14 comprises processing the set of image derived descriptors and the set of biomarker measurement values, by utilizing a set of orthogonal diagnostic methods resulting in an output signal indicative of the radiotoxicity in the area of the tissue of interest. The orthogonal diagnostic methods are characterized by that their results are not overlapping, i.e. they give complementary information (like for example morphological information from CT and inflammation status from IVD marker).

In an embodiment the output signal comprises an index, such as a diagnostic, prognostic and/or treatment-guiding index, being indicative of the probability to develop a specific side-effect.

In an embodiment, the output signal comprises multiple indices for different objectives, e.g. acute or chronic side-effects associated with the rectal wall, like rectal bleeding, rectal incontinence, acute and chronic side-effects on urinary function, e.g. stricture of urethra, urinary incontinence, etc. The indices are calculated using e.g. multivariate analysis from training data with known outcome which has been collected in clinical studies.

In an embodiment the output signal is a video signal suitable for being displayed on a display device.

In an embodiment the method further comprises adjusting the concomitant dose based on the information in the output signal. This helps minimizing complications while keeping target dose as high as possible.

In an embodiment, the processing step 14 further comprises processing questionnaire data obtained from a questionnaire database, in conjunction with the processing of the derived image descriptors and the biomarker measurement values.

In an embodiment, the questionnaire data is based on Expanded Prostate Cancer Index Composite (EPIC), which is an instrument to measure health-related life quality of prostate cancer patients. EPIC comprises a patient questionnaire with 50 questions in four domains: urinary, bowel, sexual and hormonal. Each domain summary score has distinct parts describing body function and the bother resulting from it. Factor analysis supports dividing the urinary domain summary score into two distinct subscales: incontinence and irritative/obstructive. Each EPIC question has several response options forming a Likert scale. Scores are linearly transformed to a standardized value on a 0-100 scale, with higher scores representing higher quality of life. The standardized values are averaged within the four domains to obtain summary and subscale scores.

TABLE 1

Table 1: EPIC questionnaire domains and subscales. The term "item" refers to a question in the questionnaire. "HRQOL" abbreviates health related quality of life.

| HRQOL Domain | Number if items | Mean Score (sd) | Test-retest reliability | Internal consistency reliability |
|---|---|---|---|---|
| HRQOL Domain Summary Scores | | | | |
| Urinary | 12 | 80.2 (17.5) | 0.88 | 0.88 |
| Bowel | 14 | 86.6 (15.7) | 0.84 | 0.92 |
| Sexual | 13 | 33.1 (23.6) | 0.91 | 0.93 |
| Hormonal | 11 | 86.6 (13.8) | 0.80 | 0.82 |
| Domain-Specific HRQOL Subscales | | | | |
| Urinary Subscales | | | | |
| Function | 5 | 86.5 (16.7) | 0.83 | 0.69 |
| Bother | 7 | 75.8 (20.4) | 0.87 | 0.85 |
| Incontinence* | 4 | 83.2 (22.9) | 0.87 | 0.89 |
| Irritative/Obstructive* | 7 | 79.7 (18.5) | 0.89 | 0.81 |
| Bowel Subscales | | | | |
| Function | 7 | 87.9 (13.6) | 0.78 | 0.75 |
| Bother | 7 | 85.3 (18.8) | 0.85 | 0.90 |
| Sexual Subscales | | | | |
| Function | 9 | 29.5 (24.0) | 0.90 | 0.92 |
| Bother | 4 | 41.1 (30.1) | 0.78 | 0.84 |
| Hormonal Subscales | | | | |
| Function | 5 | 84.0 (15.3) | 0.79 | 0.51 |
| Bother | 6 | 88.7 (13.6) | 0.73 | 0.73 |

*A single global urinary bother item, which does not distinguish bother related to incontinence from that related to urinary obstruction is not included in the Urinary Incontinence or Urinary Irritative/Obstructive subscales; therefore 11 urinary items comprise these 2 subscales whereas the Urinary Summary Domain includes 12 items.

Figure 2:
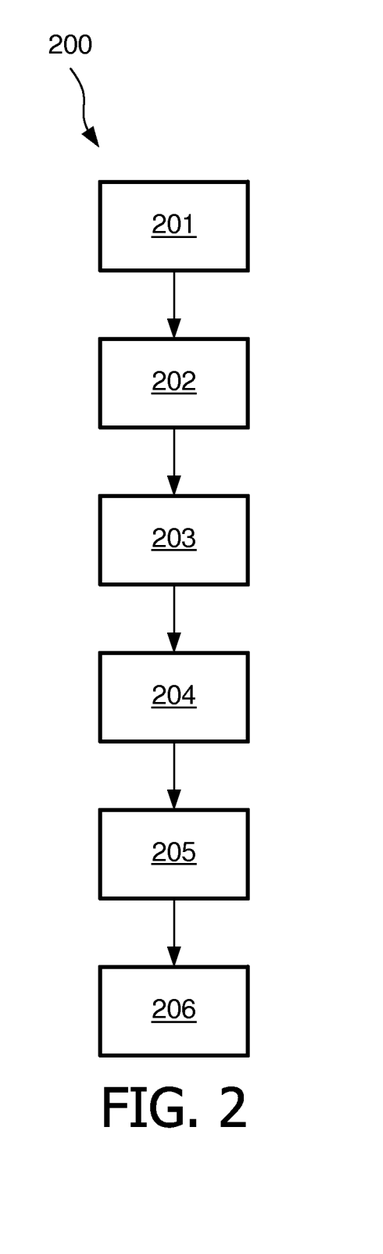
FIG. 2 is a flow chart of a method according to an embodiment.

In an embodiment, according to FIG. 2, a method 200 of producing an individual patient profile is provided. The method comprises inputting 201 data, such as individual patient answers to multiple-choice questions of a medical questionnaire and storing 202 these answers in a data file forming an individual patient profile comprising the answer selection excluding the actual question text. The method also comprises storing 203 information of the questionnaire version presented to the patient and the date of questionnaire completion in the data file. Profile processing algorithms may be used, e.g. for automatic adjustment for questionnaire version, computation of score development over time, comparison of an individual patient profile to profiles of other patients of e.g. same/different age, disease grade, medication regimen, or treatment scheme. The automatic score computation may be used for automatic flagging of patients as extra radiation sensitive or extra hit by radiation side-effects. The method 200 may also comprise checking for validity the inputted data before storing 202. For example, this may be performed during the inputting step when data is inputted, which reduced the risk of erroneous inputting of data.

An advantage of the method is that summary and subscale scores may be calculated without utilizing complex and time consuming external statistic software.

Moreover, the method provides for an easier way to quantitatively compare different patient subgroups.

Moreover, the method facilitates storing the questionnaire data, quantifying and presenting variations, defining severe radiotoxicity, and calculating responses to present in studies etc. moreover, it enables making reliable comparisons between different medical studies and different medical centers.

Furthermore, the method provides for computerized input, manipulation, retrieval, and storage of EPIC data.

The method also removes the need for manual proof reading of manually filled in questionnaires. Hence, a considerable amount of time of highly trained medical personnel is set free, and thus the workflow in the management of radiotherapy may be improved.

In an embodiment, the method comprises creating 204 a questionnaire database comprising a number of individual patent profiles represented by a corresponding number of data files. Hence, each data file may be stored in a questionnaire database.

In an embodiment, the method 200 further comprises creating 205 an individual patient profile report by applying a profile processing algorithm on the information of the data file, such as at least one of the answers. Individual patient EPIC profiles may be correlated to treatment type, treatment outcome, co-morbidities, medication, anamnetic data, and in vitro diagnostic tests results data like PSA value, cell counts, and/or CRP.

In an embodiment the method comprises displaying 206 the individual patient profile report on a display device.

With regard to the step of inputting 201 data, several possibilities exist. Of course, patients may fill out a printout of the questionnaire and hand it in to the medical personnel, who transfer the patient's answers to a computer. This step may also be simplified by using a digitalization unit (e.g. a scanner or a digital camera) and a specialized image pattern recognition algorithm to interpret the printout questionnaires and store their data in the database. Alternatively, patients may answer the questionnaire electronically on a computer or laptop situated e.g. in the office of a medical doctor, in the waiting room, or at patient's home. In the future, the computer may be replaced by a hospital or patient's PDA (Personal Digital Assistant) or palmtop. At some occasions, it may be advantageous to let patients answer the questions by calling a number and answering recorded questions by pressing the buttons of a normal telephone.

The method 200 may be utilized for therapy monitoring and individual treatment adaptation, especially for radiotherapy of prostate cancer. It may be used to assist in early detection of radiation side-effects (radiotoxicity) through automatically flagging patients suitable for or in need of dosis adaptation. Hence, the method may be used for optimization of treatment, i.e. before or during treatment.

In a practical example, each individual patient profile may comprise individual patient answers to multiple-choice questions, answered at different points in time. In an experiment each patient filled out a printout of the questionnaire at four consecutive points in time:

Time A: before EBT, at the day of radiotherapy planning
Time B: on the last day of EBT, after 7-8 weeks of 2 Gy daily (total dose 66-80 Gy)
Time C: Two months after the last day of EBT
Time D: One year after the last day of EBT At time A, each patient was given a unique six-digit identification number. The questionnaires were handed over to the patients personally by a physician. Patients were instructed to answer the questions at the specified time points and then return the answers to the present inventors.

In comparison to the standard EPIC a modified questionnaire may be used, wherein the last question is omitted. Furthermore, in an embodiment, the alternative answers of the questions of the questionnaire is re-ordered, to always start with the largest bother/lowest level of function. In the standard EPIC, the corresponding order of alternatives varies, making it prone to errors from patients as well as from medical personnel.

In an embodiment, the questionnaire database is set up using a MySQL server, wherein SQL is an abbreviation for Structured Query Language. The step of storing 202 the answer selection of an individual patient was achieved through storing of numbers representing the selections of the patient in a data file. Each questionnaire was stored as a single row in the questionnaire database.

In every questionnaire database row, each question had a separate cell to store its answer. In an embodiment, each combination of patient number and questionnaire name (A, B, C, D) is given a table-wide unique number in order to be able to address the combination using a single reference. An alternative way to store the selections of patients is to store only the selections deviating from the maximum value (lowest bother/highest life quality).

In an embodiment, EPIC input scores are input by the user (e.g. medical professional, secretary, or the patient himself) and automatically transformed to a standardized value on a 0-100 scale. Individual items (specific questions) correspond to specific item response values (1-5 or 1-4 or 1-3) and standardized values (0/25/50/75/100 or 0/33/67/100 or 0/50/100 or 0/50/100/50/0), with the highest value always indicating the lowest bother grade/highest life quality.

A linear transformation of answer n to score value s is used:

$$s(n) = (n-1) \cdot \frac{100}{N-1},$$

where s is the calculated score value, n is the encoded answer of the patient ranging from e.g. 1 to 5 and N is the number of choices for this specific question, e.g. 5. In our implementation, this transformation is implemented using a kind of look-up-table. As an example, the urinary functional score $S_{uf}$ is calculated as:

$$s_{uf} = \frac{1}{c} \sum_{i=1}^{5} s(n_i),$$

with c being the number of answered questions for this subset of questions and $n_i$ being the encoded answer for question number i. A meaningful score can only be calculated if c is greater than or equal to a threshold for the specific subset (80% of questions answered), e.g. at least 4 out of 5 for the urinary function score.

The most practicable way to store questionnaire data is to code the answers to specific questions with the respective response values. Domain summary scores and subscale scores are automatically computed and stored in the individual patient profile and added to the growing collection of the patient population for automatic computation of statistical values for comparison of various patient groups. Statistical measures, e.g. Mann-Whithney-U-test, Wilcoxon's mathed-pairs test, contingency table analysis, can be automatically implemented in order to quantify differences between patient subgroups, changes over time for individual patients, etc. Mean/median scores of the actual/relevant patient group can be displayed. Simplified input of scores can be realized by displaying earlier scores of the same patient and typing in only (potential) changes since the last input or since the first input. In a similar way, mean/median scores of the actual/relevant patient group can be displayed, so that only (potential) deviations of the individual patient to the rest of the relevant patient collective have to be typed in.

The score development over time can be automatically displayed in order for medical personnel to get a quick and comprehensible overview of the patient's quality of life and treatment side-effects for potential treatment adaption. Furthermore, the overview can be designed for easy identification of outliers (patients in a population or data points in a development over time). An automatic warning flag function can be implemented to mark e.g. outliers or e.g. patients always ticking the first or last box of all items.

Severe radiation toxicity can be defined in several ways. For example, the 20% with worst EPIC reported side-effects of an investigated patient population can be used to define a cut-off summary or function score value for severe radiotoxicity. Alternatively, patients with function and/or a summary score difference of −40 acute (score at time B minus score at time A) or −20 long term (score at time C minus score at time A) can be classified as suffering from severe radiotoxicity. These or similar differences can be automatically computed. The patient profiles indicating severe radiotoxicity can be automatically marked in the database.

Figure 3:
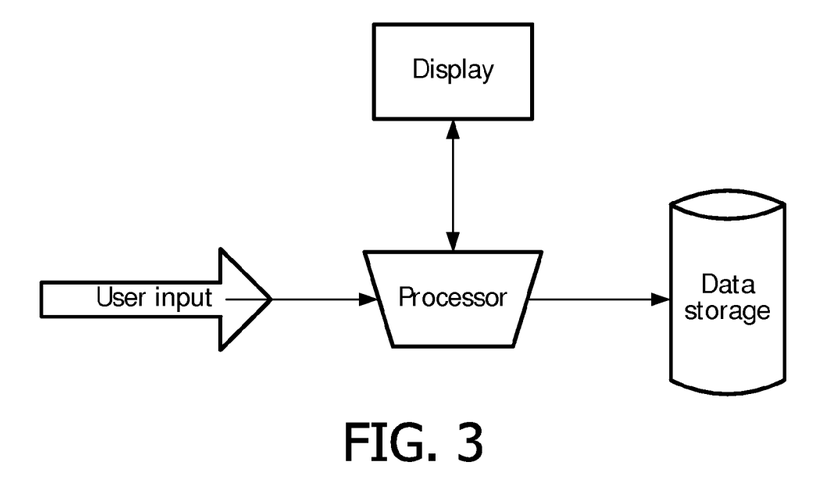
FIG. 3 is an illustration of a database system according to an embodiment.

The front-end for questionnaire input and modification was implemented using HTML. It can therefore be used with any web-browser, independent of platform. The back-end for addition and modification of questionnaires and for score calculations was implemented using the Perl programming language. For communication between the Perl back-end and the HTML front-end, XML messages and HTTP Posts were used. A simplified diagram of the questionnaire database system for individual profiles is shown in FIG. 3.

To be able to input questionnaire data or to edit already stored questionnaires it is necessary to display the question numbers and/or the stored values. A possible questionnaire to determine the quality of life experienced by the patients, contains questions like:

how often do you experience unintentional urine loss?
how often do you experience blood in your urine?
how often do you experience pain or a burning sensation while urinating?

These questions can be answered by choosing one of the following:

frequently per day;
about once per day;
frequently per week;
about once per week;
almost never.

In addition, patient can indicate how they experience these problems, like:
- it's a big problem;
- it's an average problem;
- it's a small problem;
- it's a very small problem;
- it's not a problem at all.

Alternatively, the questions can be replaced by their sequel number in the questionnaire, and the answers can be replaced by numerical values. In this way an experienced user is allowed to enter the correct answer representations very fast.

The possible questionnaire could also include a question like:
- how would you classify your ability to control your urination? Such a question can be answered by choosing one of the following:
  - no urination control
  - often occurring unintentional urine drops
  - sporadic unintentional urine drops
  - complete urination control The possible questionnaire could also include a question like:
- how many incontinence diapers do you use daily to control the unintentional urine loss? Such a question can be answered by choosing one of the following:
  - three or more daily
  - two daily
  - one daily
  - no daily The stored values are received from the database using a Perl script sending an XML message which is parsed by JavaScript code which subsequently also fills out the corresponding fields in the mask. The automatically computed scores are displayed to the user. Input questionnaires can be modified, deleted, and additional questionnaires can be added e.g. after the first one at time A. The user interfaces were designed to allow a quick and simple overview to the user and to require only a minimum of user software training.

Scores are automatically calculated from a completed questionnaire displayed to the user. A user can select a patient resulting in allowing the user to select a questionnaire for the patient to modify, delete, or evaluate can be selected. The summary scored are preferably grouped according to their relevance. For example: grouping according to "urinary", "bowel", "sexual", "hormonal". Data anonymization is a crucial issue for clinical applications, e.g. to render possible data analysis at sites outside the hospital. Two export functions from the database allow the user to export anonymized data. Hereby, patient names and birthday are removed, whereas the six-digit patient number and year of birth are kept. To allow an easy way of anonymizing the data in the database, the table storing personal patient information (patient number, name, birthday, etc.) may be split up into two tables. One of the tables incorporates the private patient data and the unique six-digit patient number. The other table includes only non-private patient data. During export, all tables except the table comprising private data are saved to an SQL file. The second export function generates a CSV file of the individual patient profiles in the database, sorted by date and time. For such overviews, all or a selection of fields can be picked out.

The score values of each answer in the individual patient profiles, which are stored in the created questionnaire database, may be processed in the processing step 14 in conjunction with the first set of image derived descriptors, and the measured biomarker values, resulting in an output signal indicative of the radiotoxicity of the area of the tissue of interest which is to be subject to radiation therapy.

The summary and subscale scores for each individual patient profile may be calculated immediately as soon as the answers are entered in the database. The results can be directly obtained without the need to repeatedly use complicated algorithms, enabling a quick overview, and eliminating unnecessary sources of errors.

The questionnaire database or the individual patient profiles are not limited only to the use of the EPIC classification system, but any other classification system, such as RTOG/EORTC-CTC score (Radiation Therapy and Oncology Group/European Organization for Research and Treatment of Cancer—Common Toxicity Criteria) for radiation therapy, may be used. Correlations and discrepancies between the patient reported EPIC and the physician reported RTOG/EORTC may be automatically detected, quantified and reported.

Figure 4:
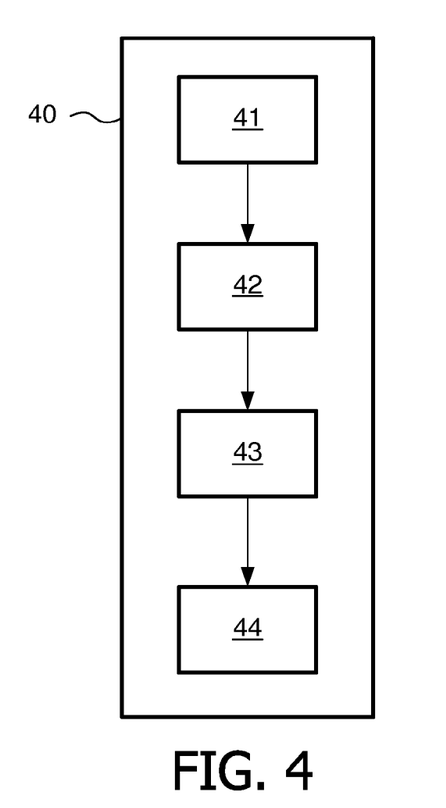
FIG. 4 is block diagram of a computer program product according to an embodiment.

In an embodiment, according to FIG. 4 a computer program product 40 is provided. The computer program product is configured to perform the steps of the method according to some embodiments, and may be used as a clinical decision support system (CDSS) utilizing a database of any kind, and configured to correlate imaging descriptors and biomarker information with radiotoxicity measures.

The computer program product 40 has embodied thereon a computer program for processing by a data-processing apparatus. The computer program comprises a first code segment 41 for obtaining at least one image-derived descriptor from an image modality, wherein the image derived descriptor pertains to a tissue of interest for which radiotherapy is planned or a tissue in the vicinity of this target volume. The computer program further comprises a second code segment for selecting at least one disease specific biomarker suitable for detecting or quantifying radiotherapy side-effects in the area of the tissue of interest. Furthermore, the computer program comprises a third code segment 43 for retrieving at least one measurement value of the selected disease specific in vitro diagnostic biomarker. Moreover, the computer program comprises a fourth code segment 44 for processing the at least one image derived descriptor and the at least one disease specific in vitro diagnostic biomarker measurement value by means of a correlation technique, resulting in an output signal indicative of the radiotoxicity in the area of the tissue of interest.

In an embodiment the computer program comprises code segments arranged to perform any of the steps in the method according to some embodiment.

The computer program is configured to be run on a data processing apparatus, such as a processor.

The output signal provides an estimate of severity of side-effects. From output signal a recommendation as to how the radiotherapy should be adapted to minimize side-effects or even as to which treatment is to be selected for an individual patient may be extracted. The computer program product may be distributed, i.e. it may actually involve multiple application software packages on multiple computer systems. One of these application packages may be used to evaluate image information, e.g. analyze image data to derive information required by the step of processing 14, 44. This may involve automatic or manual segmentation of tumor target and risk organs to generate mask volumes. This may also involve more complex tasks of image analysis, for instance the calculation of perfusion parameters from dynamic image sequences as in DCE-MRI. Another application package may involve radiotherapy planning to generate dose calculations. A further application software and computer system may deal with data storage, e.g. a DICOM based picture archiving system (PACS). Yet another computer system and application package may involve the calculation and storage of in vitro diagnostic data like mass spectra. Finally, a further computer system and application package may provide the interfacing to the different data sources, computer systems and application software packages. This last system preferably provides the integrated analysis software package that performs the data analysis of the feature vectors as described in the method above.

In a practical example, during radiotherapy, the side-effects detected by the individual patient is monitored by means of the computer program product. The acute scores are computed, extra radiation sensitive individuals are automatically flagged in order to modify (or even discontinue) the radiotherapy (e.g. no radiation boost). Patients with function and/or a summary score difference of −40 acute (score at time B minus score at time A) or −20 long term (score at time C minus score at time A) can be classified and flagged as suffering from severe radiotoxicity. Here, B is a time point during the therapy (not after) and therefore allows for therapy modification before side-effects get too severe.

In an embodiment the method or computer program product according to some embodiments is implemented in a medical workstation or medical system, such as a Radiation Treatment System, Computed Tomography (CT) system, Magnetic Resonance Imaging (MRI) System or Ultrasound Imaging (US) system.

The invention may be implemented in any suitable form including hardware, software, firmware or any combination of these. However, preferably, the invention is implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method (10) for radiotherapy monitoring, comprising:
   obtaining (11) at least one image derived descriptor from an image modality, wherein the image derived descriptor pertains to a tissue of interest for which radiotherapy is planned or a tissue in the vicinity of this target volume,
   selecting (12) at least one disease specific biomarker suitable for detecting or quantifying radiotherapy side-effects in the area of the tissue of interest,
   retrieving (13) at least one measurement value of the selected disease specific in vitro diagnostic biomarker, and
   processing (14) the at least one image derived descriptor and the at least one disease specific in vitro diagnostic biomarker measurement value by means of a correlation technique, resulting in an output signal indicative of the radiotoxicity in the area of the tissue of interest.

2. The method according to claim 1, wherein the step of processing comprises compressing the at least one image derived descriptor before correlation with the at least one disease specific in vitro diagnostic biomarker measurement value.

3. The method according to claim 1, wherein the step of processing is further performed by calculating treatment-guiding indices of the side-effects based on the output signal.

4. The method according to claim 1, wherein the step of processing (14) further comprises calculating an index indicative of grade of radiotoxicity by means of multivariate analysis.

5. The method according to claim 1, wherein the disease specific in vitro diagnostic biomarker is selected from the group comprising: haemoglobin concentration (Hb), complete and leukocyte blood cell count, C-reactive protein (CRP), ferritin, transferrin, creatinine, alpha-amylase, HbA1c, TNF-α, lactate dehydrogenase (LDH), interleukins, hepcidin, pro-hepcidin, immunoglobin fragments, or citrulline.

6. The method according to claim 1, wherein the image-derived descriptor is selected from the group comprising:
   macroscopic tumor volume; risk organ; volumetric information either directly assessed by the imaging modality by means of Hounsfield units of CT data or dose deposition volumes calculated by the radiotherapy planning software, or indirectly assessed by the imaging modality by means of parametric maps derived from dynamic imaging sequences or DVH data.

7. The method according to claim 3, wherein the step of obtaining (11) comprises obtaining a first feature vector comprising the obtained image derived descriptors, and the step of retrieving (13) results in a second feature vector comprising the retrieved selected disease specific in vitro diagnostic biomarker measurement values, and wherein the first and second feature vector are processed in the step of processing (14).

8. The method according to claim 7, wherein the step of processing (14) is further performed by
   composing a number of sub feature vectors from the first or second feature vectors,
   analyzing each sub feature vector for a scalar result, and
   processing the scalar results jointly and calculating sub indices for each combination of sub feature vectors.

9. The method according to claim 1, wherein the output signal is a video signal suitable for being displayed on a display device.

10. The method according to claim 1, wherein said processing step further comprises processing questionnaire data.

11. A computer program product (40) having embodied thereon a computer program for processing by a data-processing apparatus, wherein the computer program comprises:
   a first code segment (41) for obtaining at least one image-derived descriptor from an image modality, wherein the image derived descriptor pertains to a tissue of interest for which radiotherapy is planned or a tissue in the vicinity of this target volume, a second code segment (42) for selecting at least one disease specific biomarker suitable for detecting or quantifying radiotherapy side-effects in the area of the tissue of interest, a third code segment (43) for retrieving at least one measurement value of the selected disease specific in vitro diagnostic biomarker, and a fourth code segment (44) for processing the at least one image derived descriptor and the at least one disease specific in vitro diagnostic biomarker measurement value by means of a correlation technique, resulting in an output signal indicative of the radiotoxicity in the area of the tissue of interest.

* * * * *